United States Patent
Cao

(10) Patent No.: US 7,192,278 B2
(45) Date of Patent: Mar. 20, 2007

(54) BASE ASSEMBLY FOR FABRICATION OF FALSE TEETH

(75) Inventor: Guodong Cao, Shandong (CN)

(73) Assignee: Qingdao Donghe Denture, Shandong (CN)

( * ) Notice: Subject to any disclaimer, the term of this patent is extended or adjusted under 35 U.S.C. 154(b) by 0 days.

(21) Appl. No.: 11/201,200

(22) Filed: Aug. 11, 2005

(65) Prior Publication Data
US 2006/0228666 A1 Oct. 12, 2006

(30) Foreign Application Priority Data
Apr. 7, 2005 (CN) .................. 2005 2 0011525 U

(51) Int. Cl.
*A61C 11/00* (2006.01)
(52) U.S. Cl. .......................... 433/60; 433/74
(58) Field of Classification Search ................. 433/74, 433/60, 213
See application file for complete search history.

(56) References Cited

U.S. PATENT DOCUMENTS

| | | | | |
|---|---|---|---|---|
| 3,478,428 A | * | 11/1969 | Stengel | 433/74 |
| 4,203,219 A | * | 5/1980 | Wiener | 433/74 |
| 4,238,189 A | * | 12/1980 | Tirino | 433/74 |
| 4,265,619 A | * | 5/1981 | Lucki et al. | 433/54 |
| 5,611,686 A | * | 3/1997 | Silva | 433/74 |
| 5,658,143 A | * | 8/1997 | Kuperman | 433/60 |
| 5,775,899 A | * | 7/1998 | Huffman | 433/60 |
| D452,566 S | * | 12/2001 | Huffman | D24/176 |
| 6,402,513 B1 | * | 6/2002 | Sim | 433/57 |
| 2002/0031743 A1 | * | 3/2002 | Kim | 433/74 |
| 2002/0164556 A1 | * | 11/2002 | Huffman | 433/60 |

* cited by examiner

*Primary Examiner*—Ralph A. Lewis
(74) *Attorney, Agent, or Firm*—Baker & Hostetler LLP

(57) ABSTRACT

A base assembly for fabrication of false teeth includes a base, and a gum-like raised portion is provided on the said base, a plurality of protruding blocks are provided symmetrically and evenly at the interior and exterior arc edges on the raised portion, and positioning holes are provided between two opposite protruding blocks; a removable holddown plate with a configuration corresponding to the said raised portion is provided over the raised portion, and the holddown plate has a flat surface on the upper surface, has the recesses corresponding to the protruding blocks to be engaged with the protruding blocks and the mounting pins corresponding to the positioning holes to be engaged with the positioning holes on the lower surface. The time to fabricate false teeth is largely reduced and the fabrication accuracy of the false teeth is improved by using the base assembly of the present invention.

6 Claims, 3 Drawing Sheets

BASE ASSEMBLY FOR FABRICATION OF FALSE TEETH

TECHNICAL FIELD

The present invention relates to a base assembly for fabrication of false teeth, particularly to a base assembly with a removable holddown plate.

RELATED ART

At present, the plaster base is widely used for the fabrication of false teeth in the dental surgery. And the process is grinding the bottom of the plaster cast of a tooth obtained by a dentist, then drilling a hole on the bottom and inserting a metal nail into the drilled hole to bond, placing the cast with the nail in the plaster base which is blended well but not concrete for 24 hours, and after the plaster is completely hardened, taking it out for use in postprocessing. The drawbacks of this kind of plaster base are that (1) the fabrication process costs a long time, needing 24 hours from modifying cast, drilling the hole, bonding the nail till hardening the base; (2) the bonding strength between the metal body and the plaster tooth cast is weak and they are easy to disjoin, so the bad fixing effect is easy to cause a displacement, thereby affecting the processing accuracy of the false tooth; and (3) a separating agent layer with a certain thickness must be applied when fixing the tooth cast and the base to each other, and the separating agent is easy to shed during the separating process so as to cause the height error of the teeth in the tooth cast, thereby affecting the accuracy of the false teeth.

SUMMARY OF THE INVENTION

To overcome the drawbacks of the prior art, the present invention provides a base assembly with a removable holddown plate, which largely reduces the fabrication time and improves the fabrication accuracy of false teeth.

To achieve the above objects, the present invention is carried out through the following technical solution.

A base assembly for fabrication of false teeth includes a base, and a gum-like raised portion is provided on the said base, a plurality of protruding blocks are provided symmetrically and evenly at the interior and exterior arc edges on the raised portion, and positioning holes are provided between two opposite protruding blocks.

A removable holddown plate with a configuration corresponding to the said raised portion is provided over the raised portion, and the holddown plate has a flat surface on the upper surface, has the recesses corresponding to the protruding blocks to be engaged with the protruding blocks and the mounting pins corresponding the positioning holes to be engaged with the positioning holes on the lower surface.

Detchable positioning pins are provided on the upper surface of the said holddown plate opposite to the mounting pins of the lower surface. The positioning pins are embedded in the plaster tooth cast and perform the positioning function.

The positioning pins are secured through the threaded connecting portion provided on the top of the mounting pins.

A jaw support fixing groove is provided at a side of the said base. The said protruding blocks at the exterior arc edge of the raised portion are in the shape of semicircle, while the protruding blocks at the interior arc edge are in a U-shape.

The said positioning holes are two or more rows of parallel circular holes.

The positioning holes are a single row of square holes, trigonal holes, rectangular holes or rhombic holes.

The said mounting pins are made of metal or organic materials.

The merits of the present invention are as follows:

1. The process time is largely reduced, taking only 30 minutes. Since a removable holddown plate is utilized to assemble with a base so that the tooth cast can be adhered to the holddown plate, the process can be carried out after the adhesive is cured, thereby reducing the process time largely.

2. The mounting pins are embedded in the holddown plate by compression casting, and can be assembled accurately and fixedly with the base, so the retention strength is strong and it is not easy to drop out, thereby enhancing the resistance to the pulling force largely.

3. Since the upper surface of the holddown plate is a flat surface with the positioning pins, the tooth cast can be bonded to the holddown plate completely and seamlessly only by adhering after grinding the bottom of the tooth cast, and can improve the process accuracy of the false teeth by matching with the positioning pins which are embeded into the plaster tooth cast and perform the positioning function.

4. There is no deformation, steady and has a good positioning effect, and occurs little displacement.

5. Accurate positioning, high precision. The holddown plate can be accurately positioned on the base through the engagements of the recess on the holddown plate with the protruding blocks on the base, and of the mounting pins on the holddown plate with the positioning holes on the base.

6. Having various applications. The process of the present invention is applicable to solid materials, such as plaster, plastic, metal, organic high molecular materials, chemical industry materials and etc.

Figure 1:
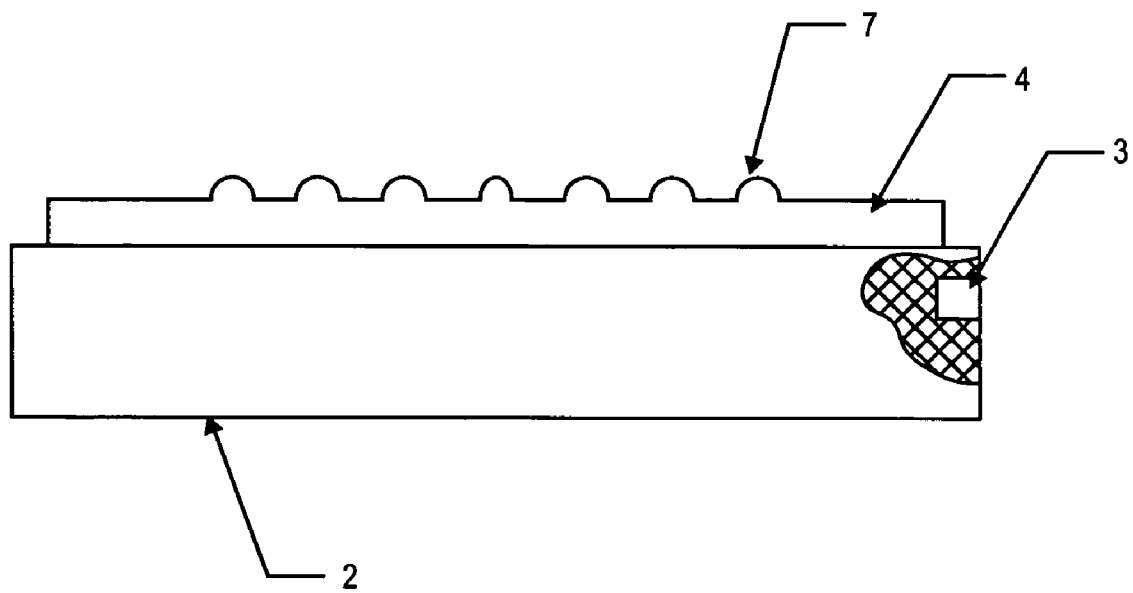
FIG. 1 is an illustrative structural view of the base according to an embodiment of the present invention.
Figure 2:
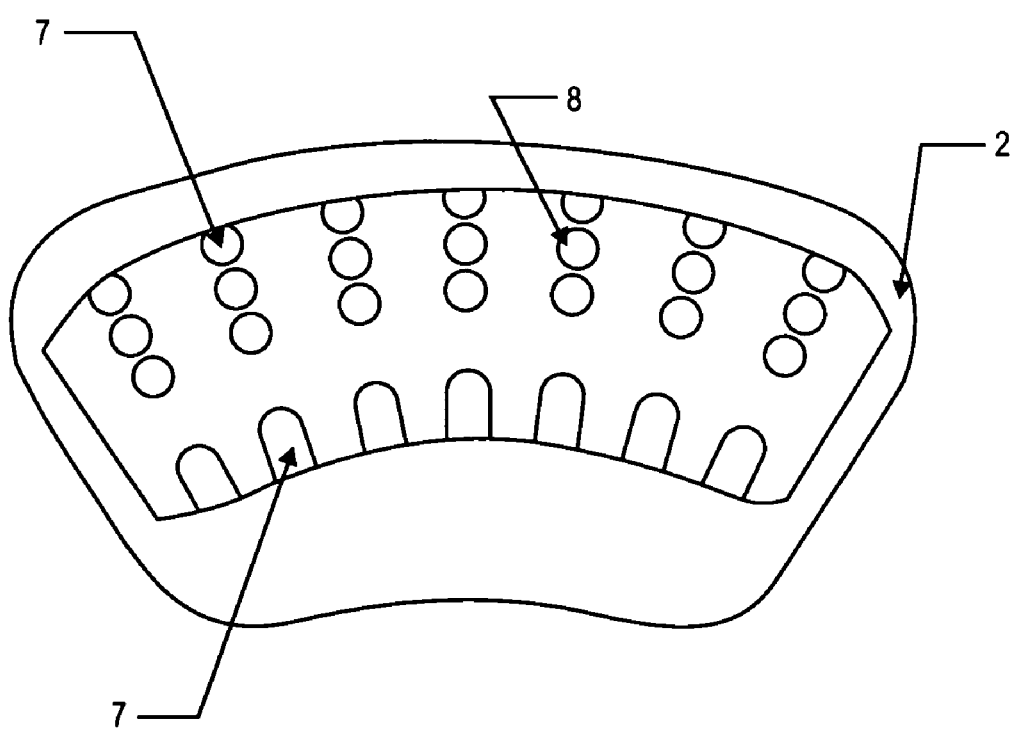
FIG. 2 is top view of FIG. 1.

Description of the reference numerals: 1. holddown plate, 2. Base, 3. jaw support fixing groove, 4. raised portion, 5. recess, 6. mounting pin, 7. protruding block, 8. positioning pin, 9. tooth cast

DETAILED DESCRIPTION OF THE PREFERRED EMBODIMENTS

The present invention will now be described in detail in combination with the embodiments and the accompanying drawings.

Figure 3:
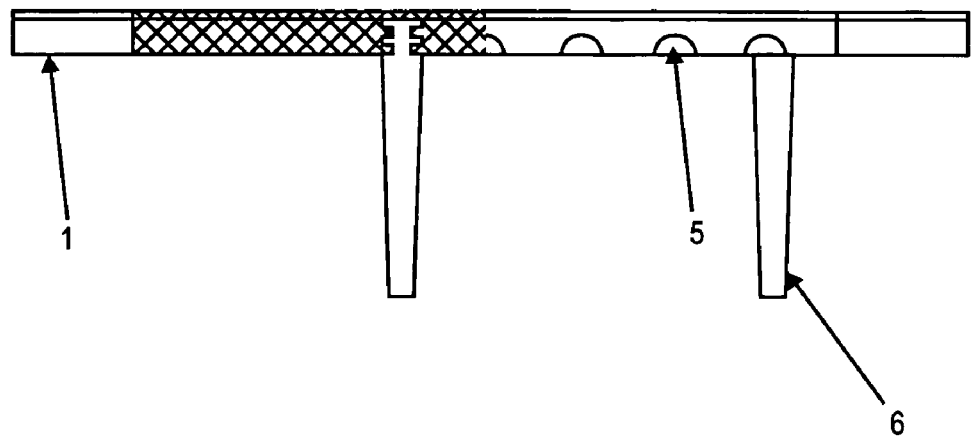
FIG. 3 is an illustrative structural view of the holddown plate according to the embodiment shown in FIG. 1.
Figure 4:
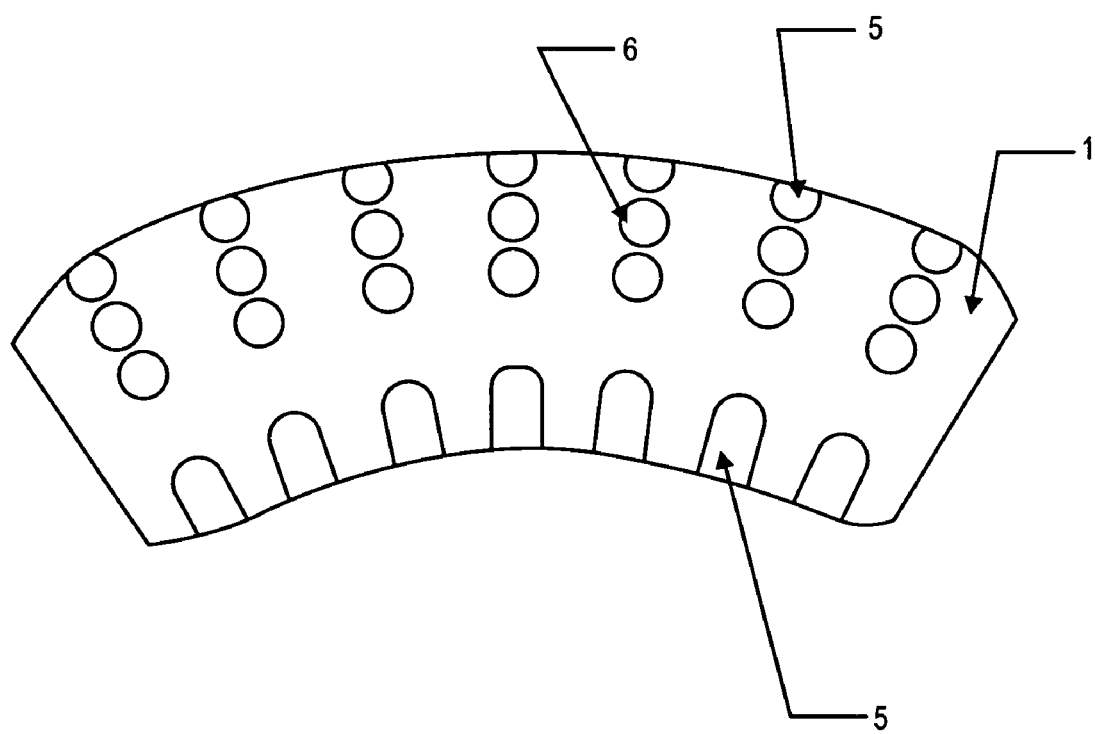
FIG. 4 is a bottom view of FIG. 3.

The base assembly for fabrication of false teeth shown in FIG. 1 to FIG. 4 includes a base 2 which is generally made of plaster. A gum-like raised portion 4 is provided on the base 2, a number of protruding blocks 7 are provided symmetrically and evenly at the interior and exterior arc edges of the raised portion 4, and positioning holes 8 are provided between two opposite protruding blocks 7; a removable holddown plate 1 with a configuration corresponding to the said raised portion 4 is provided over the raised portion 4, and the holddown plate 1 has a flat surface on the upper surface, has the recesses 5 corresponding to the protruding blocks 7 to be engaged with the protruding blocks 7 and the mounting pins 6 corresponding the positioning holes 8 to be engaged with the positioning holes 8 on the lower surface. In the present example, the protruding blocks 7 at the exterior arc edge of the protruding portion have 7 in number and are in the shape of semicircle, while the protruding blocks 7 at the interior arc edge which are opposite to the protruding blocks 7 at the exterior arc edge have also 7 in number and are in a U-shape. Two rows of circular positioning holes are provided parallel between the two opposite protruding blocks, having 14 in total number. And on the holddown plate, provided with the recesses corresponding to the protruding blocks are provided to engage with the protruding blocks, and two rows of mounting pins corresponding to the positioning holes are provided parallelly to engage with the positioning holes (only two mounting pins are shown in FIG. 3, and the others are not shown). The holddown plate and the mounting pins can be fixed together with two kinds of materials by compression casting, or can also be formed integrally with one kind of material. With this structure, the holddown plate can be taken out or inserted into the base freely, and can be accurately secured on the base by the engagements of the protruding blocks with the recesses and the positioning holes with the mounting pins, thereby preventing the displacement between the holddown plate and the base.

Figure 5:
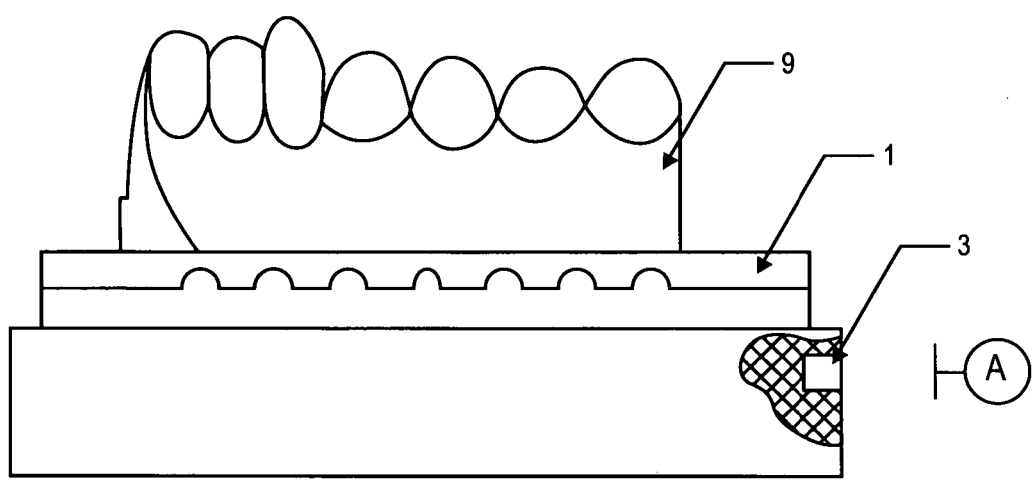
FIG. 5 is a working state of the present invention.

As shown in FIG. 5, when in use, it is only necessary to grind the bottom of the tooth cast flat and adhere it to the holddown plate 1. When processing the false tooth, the tooth cast portion of the false tooth is cut off together with the holddown plate, and the holddown plate with the fabricated false tooth can be inserted back into the base at any time during the fabrication to revise the false tooth. With this structure, the processing time is largely reduced and the fabrication accuracy of the false tooth is improved.

With the same structure, the detachable positioning pins are provided on the upper surface of the holddown plate opposite to the mounting pins on the lower surface. When fabricating the false tooth in a certain position, there may leave only the positioning pins in the said position, and remove the positioning pins in the other positions. The positioning pins are embedded in the plaster tooth cast to perform the positioning function, and further ensure the positioning of the tooth cast besides the adherence and securing between the tooth cast and the holddown plate, thereby improving the process accuracy of the false tooth. The positioning pins can be secured through the threaded connecting portion provided on the top portion of the mounting pins. When making the mounting pins, the nut-like threaded connecting portion can be machined on the top, and threads for matching with the threaded connecting portion can be machined at the corresponding connecting portions of the positioning pins. The positioning pins can be screwed on when it is necessary to provide the positioning pins in a relevant position. So, not only the position relationship of the false tooth cast portion at the false tooth's position and the entire tooth cast can be ensured, but also the displacement between the the tooth cast portion at the false tooth's position and the holddown plate can be prevented, thereby improving the process accuracy of the false tooth largely.

With the same structure, a jaw support fixing groove 3 can be provided on a side of the base to install and connect a base with the same structure for fabricating the false tooth of the upper teeth.

With the same structure, the positioning holes can be formed parallelly into three rows of circular holes if necessary so that the holddown plate can be more accurately positioned on the base.

With the same structure, the positioning holes can be a single row of square holes, trigonal holes, rectangular holes or rhombic holes which also functions to prevent the rotation between the holddown plate and the base.

With the same structure, the said mounting pins can be made of a material with higher rigidity, and can be made of metal materials or organic materials. The fixation between the holddown plate and the mounting pins can be carried out by integrally moulding or compression casting. In the present example, the mounting pins is the metal pins while the holddown plate is made of plastic, and the mounting pins are embedded in the holddown plate by compression casting, so improving the mounting strength, preventing falling off and enhancing the resistance to the pulling force.

What is claimed is:

1. A base assembly for fabrication of false teeth, including a base, comprising:
    a raised portion in the shape of a gum provided on the said base, a number of protruding blocks provided symmetrically and evenly at the interior and exterior arc edges of the raised portion, and positioning holes provided between two opposite protruding blocks; and
    a removable holddown plate with a configuration corresponding to the raised portion provided over the raised portion, and wherein the holddown plate has a flat surface on the upper surface, has recesses corresponding to the protruding blocks to be engaged with the protruding blocks and has mounting pins corresponding to the positioning holes to be engaged with the positioning holes on the lower surface, wherein detachable positioning pins are provided on the upper surface of the said holddown plate opposite to the mounting pins of the lower surface, and the positioning pins are secured through the threaded connecting portion provided on the top of the mounting pins.

2. The base assembly for fabrication of false teeth according to claim 1, which characterized in that, a jaw support fixing groove is provided at a side of the said base.

3. The base assembly for fabrication of false teeth according to claim 1, which characterized in that, the said protruding blocks at the exterior arc edge of the raised portion are in the shape of semicircle, while the protruding blocks at the interior arc edge are in a U-shape.

4. The base assembly for fabrication of false teeth according to claim 1, which characterized in that, the said positioning holes are two or more rows of parallel circular holes.

5. The base assembly for fabrication of false teeth according to claim 1, which characterized in that, the positioning holes are a single row of square holes, trigonal holes, rectangular holes or rhombic holes.

6. The base assembly for fabrication of false teeth according to claim 1, which characterized in that, the said mounting pins are made of metal or organic materials.

* * * * *